United States Patent
Clawson et al.

(10) Patent No.: US 12,128,232 B2
(45) Date of Patent: Oct. 29, 2024

(54) BURR HOLE PLUG

(71) Applicant: LONGEVITI NEURO SOLUTIONS LLC, Baltimore, MD (US)

(72) Inventors: Corbin Clawson, Hampstead, MD (US); Jimmy Shah, Hunt Valley, MD (US); Bradley Rabinovitz, Severna Park, MD (US)

(*) Notice: Subject to any disclaimer, the term of this patent is extended or adjusted under 35 U.S.C. 154(b) by 174 days.

(21) Appl. No.: 17/643,508

(22) Filed: Dec. 9, 2021

(65) Prior Publication Data
US 2022/0184383 A1 Jun. 16, 2022

Related U.S. Application Data

(60) Provisional application No. 63/123,547, filed on Dec. 10, 2020.

(51) Int. Cl.
*A61N 1/05* (2006.01)
*A61B 90/10* (2016.01)

(52) U.S. Cl.
CPC ............ *A61N 1/0539* (2013.01); *A61B 90/10* (2016.02); *A61B 2090/103* (2016.02)

(58) Field of Classification Search
CPC ....... A61N 1/0539; A61B 90/10; A61B 90/11; A61B 90/14; A61B 2090/103; A61M 39/0247; A61M 2039/025; A61M 2039/0261; A61M 2039/0264; A61M 2039/0279; A61M 2039/0288; A61M 25/02; A61M 2025/0246; A61M 2025/028; A61M 2210/0687
See application file for complete search history.

(56) References Cited

U.S. PATENT DOCUMENTS

| | | |
|---|---|---|
| 5,464,446 A | 11/1995 | Dreessen et al. |
| 7,204,840 B2 | 4/2007 | Skakoon et al. |
| 7,302,298 B2 | 11/2007 | Lowry et al. |
| 7,548,775 B2 | 6/2009 | Kipke et al. |
| 7,647,097 B2 | 1/2010 | Flaherty et al. |
| 8,038,685 B2 | 10/2011 | Bedenbaugh |
| 8,152,792 B1 | 4/2012 | Kornel |
| 8,603,038 B2 | 12/2013 | Nelson |
| 8,676,328 B2 | 3/2014 | Sauter-Starace et al. |
| 9,101,756 B1 | 8/2015 | Pianca et al. |
| 9,457,180 B2 | 10/2016 | Bucholz |
| 9,675,783 B2 | 6/2017 | Asaad et al. |
| 2005/0182420 A1* | 8/2005 | Schulte ............... A61N 1/0539 606/130 |
| 2009/0088826 A1* | 4/2009 | Bedenbaugh ......... A61B 90/11 607/116 |
| 2012/0316628 A1* | 12/2012 | Lopez .................... A61B 90/10 607/116 |
| 2013/0304216 A1 | 11/2013 | Paspa et al. |
| 2014/0073859 A1 | 3/2014 | Schorn |
| 2016/0263361 A1 | 9/2016 | Vadivelu et al. |
| 2017/0361069 A1 | 12/2017 | Romolo et al. |
| 2018/0132961 A1* | 5/2018 | van Venrooij ......... A61B 90/10 |
| 2022/0134090 A1 | 5/2022 | Boughner |

* cited by examiner

*Primary Examiner* — Robert A Lynch
(74) *Attorney, Agent, or Firm* — Welsh Flaxman & Gitler LLC

(57) ABSTRACT

A burr hole plug includes a base member shaped and dimensioned for position withing an aperture defined by a burr hole and a cover member shaped and dimensioned for placement over the base member to fully close the bur hole and retain a stimulation lead passing through the burr hole in place.

28 Claims, 11 Drawing Sheets

BURR HOLE PLUG

CROSS REFERENCE TO RELATED APPLICATION

This application claims the benefit of U.S. Provisional Application Ser. No. 63/123,547, entitled "BURR HOLE PLUG," filed Dec. 10, 2020, which is incorporated herein by reference.

BACKGROUND OF THE INVENTION

1. Field of the Invention

The invention relates to burr hole plugs.

2. Description of the Related Art

Burr hole covers are used in conjunction with a variety of surgical procedures requiring access to the brain. The procedures generally require the formation of a "burr hole" within the cranium. Burr holes are small holes (commonly approximately 14 mm in diameter, although other sizes are known to be used) that a neurosurgeon makes in the skull for various procedures. The burr hole allows surgeons to access the brain for the desired procedure. For example, burr holes are commonly used in conjunction with deep brain stimulation procedures where a stimulation lead is implanted within the brain to position electrodes adjacent to predetermined tissue of the brain. The electrodes are then used to electrically stimulate the tissue of the brain for the treatment of a specific disease or disorder. The stimulation lead is commonly passed through a burr hole. It is often necessary to keep the stimulation lead in position for an extended period of time. As such, it is important that the burr hole is covered and that the stimulation lead is securely retained in position during this period of time.

A need, therefore, exists for a burr hole cover providing a convenient, reliable, and effective solution to both covering the burr hole and maintaining the stimulation lead in position.

SUMMARY

In one aspect a burr hole plug includes a base member shaped and dimensioned for positioning within an aperture defined by a burr hole and a cover member shaped and dimensioned for placement over the base member to close the burr hole and retain a stimulation lead passing through the burr hole in place.

In some embodiments the base member is substantially cylindrical and includes an annular frame member defining an outer perimeter of the base member.

In some embodiments the annular frame member includes an upper surface, a lower surface, an inner sidewall extending between the upper surface and the lower surface along an aperture defined by an interior of the annular frame member, and an outer sidewall extending between the upper surface and the lower surface of the annular frame member.

In some embodiments the base member further includes at least one passageway for passage of stimulation leads through the base member.

In some embodiments the at least one passageway is defined by a plurality of inwardly directed flange members extending inwardly toward a center of the annular frame member.

In some embodiments each flange member is provided with a support beam along its upper surface.

In some embodiments the cover member is disk shaped and includes an upper surface, a lower surface, and a perimeter sidewall extending between the upper surface and the lower surface along an edge of the cover member.

In some embodiments the lower surface of the cover member is formed with a plurality of radially extending slots.

In some embodiments the slots are oriented as spokes that extend from the outer perimeter sidewall and that terminate at a central cavity located at the center of the cover member.

In some embodiments the edge of the cover member is further provided with cutouts in alignment with the radially extending slots.

In some embodiments the base member includes an outwardly extending tab member to prevent the base member from plunging into the burr hole.

In some embodiments the base member is made of porous polyethylene, expanded polytetrafluoroethylene, silicone, polymethyl methacrylate, or polyether ether ketone.

In some embodiments the cover member is made of porous polyethylene, titanium, expanded polytetrafluoroethylene, silicone, polymethyl methacrylate, or polyether ether ketone.

In some embodiments the base member and cover member are made of different materials.

In some embodiments the cover member is disk shaped and includes an upper surface, a lower surface, and a perimeter sidewall extending between the upper surface and the lower surface along an edge of the cover member.

In some embodiments the lower surface of the cover member is formed with a plurality of radially extending slots.

In some embodiments the slots are oriented as spokes that extend from the outer perimeter sidewall and that terminate at a central cavity located at a center of the cover member.

In some embodiments the edge of the cover member is further provided with cutouts in alignment with the radially extending slots.

Other objects and advantages of the present invention will become apparent from the following detailed description when viewed in conjunction with the accompanying drawings, which set forth certain embodiments of the invention.

DESCRIPTION OF THE EMBODIMENTS

Figure 1:
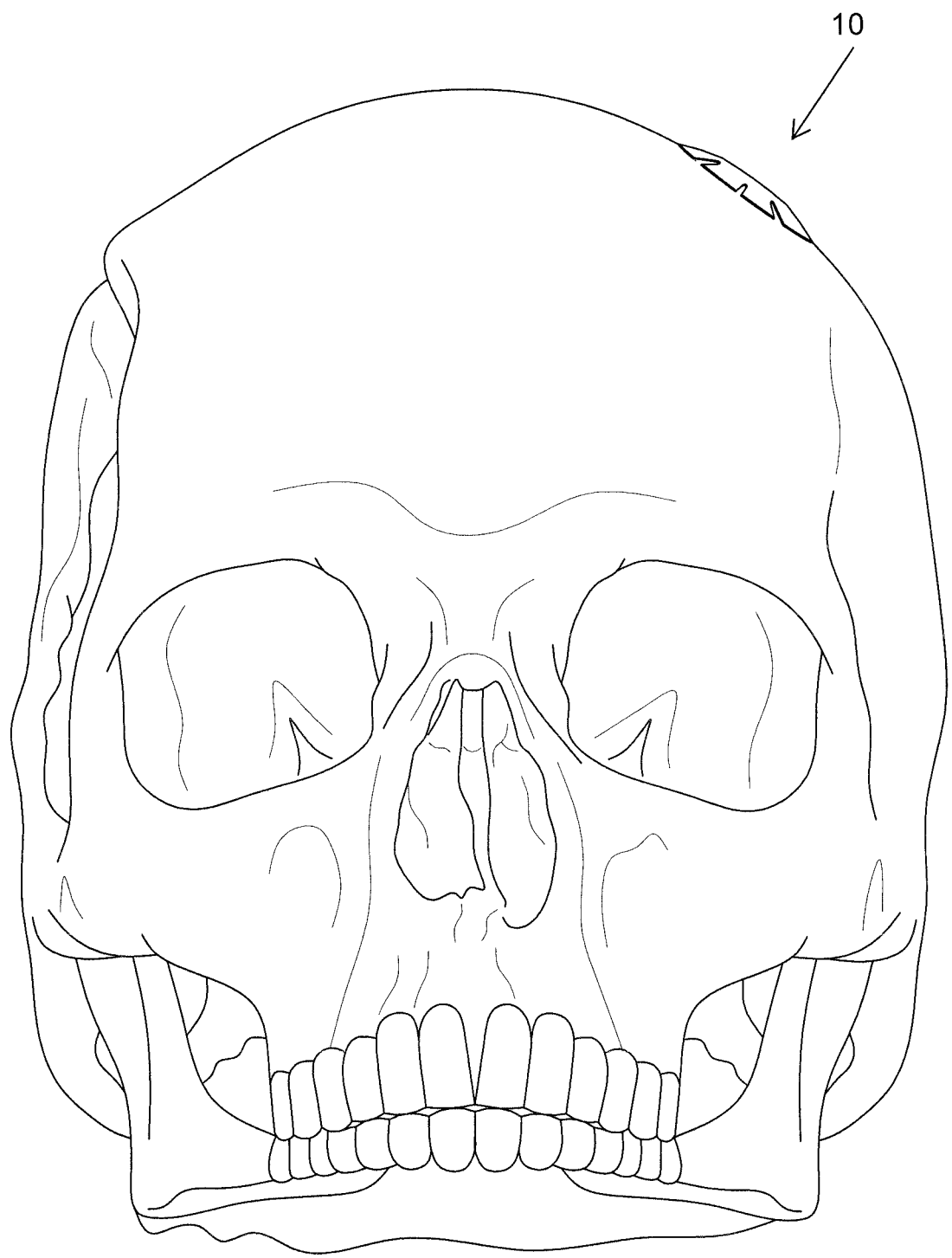
FIG. 1 is a front elevation view of burr hole plug installed within a cranium.
Figure 2:
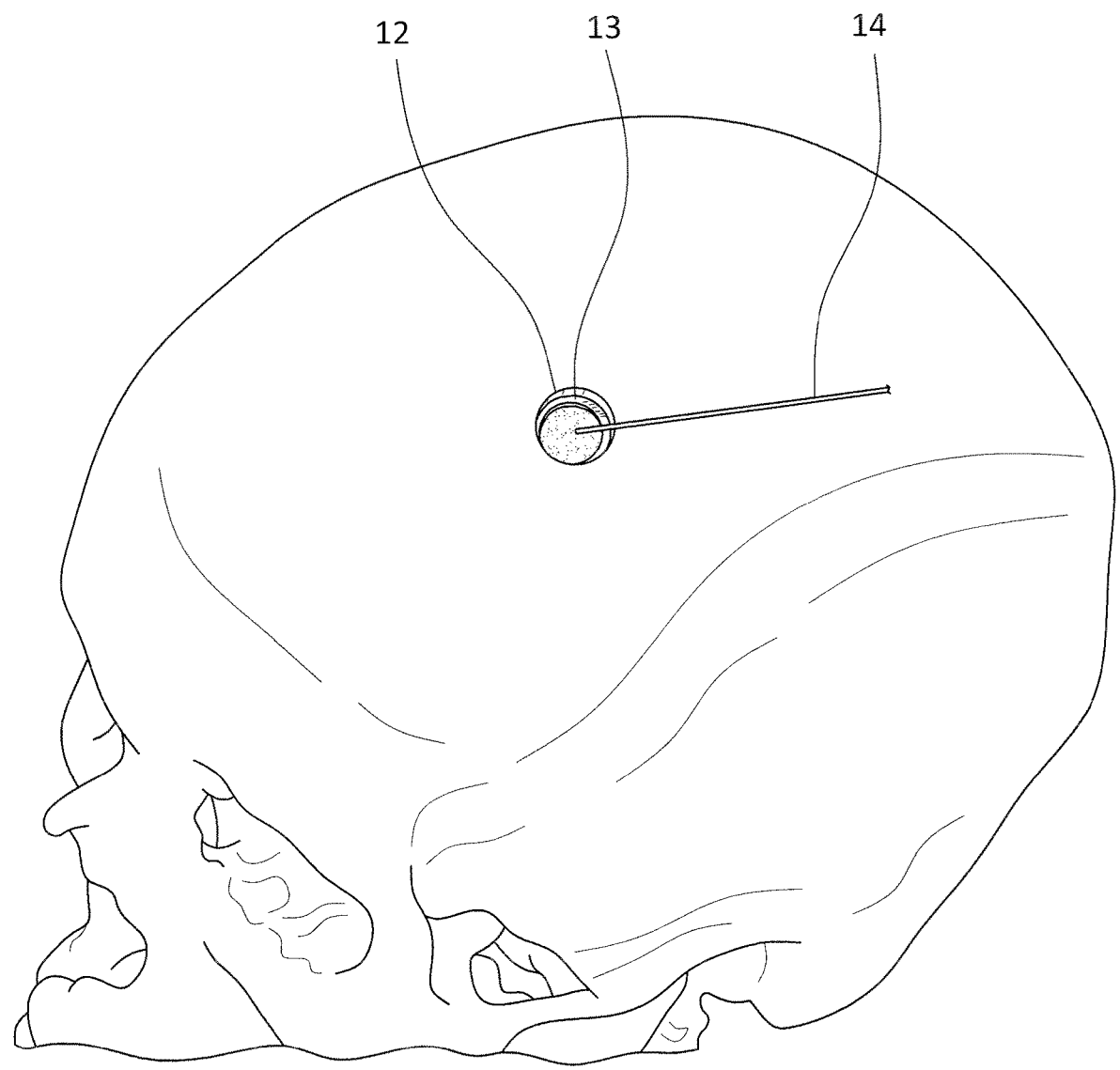
FIGS. 2, 3, 4, and 5 disclose the sequence of steps in the installation of the burr hole plug.
Figure 3:
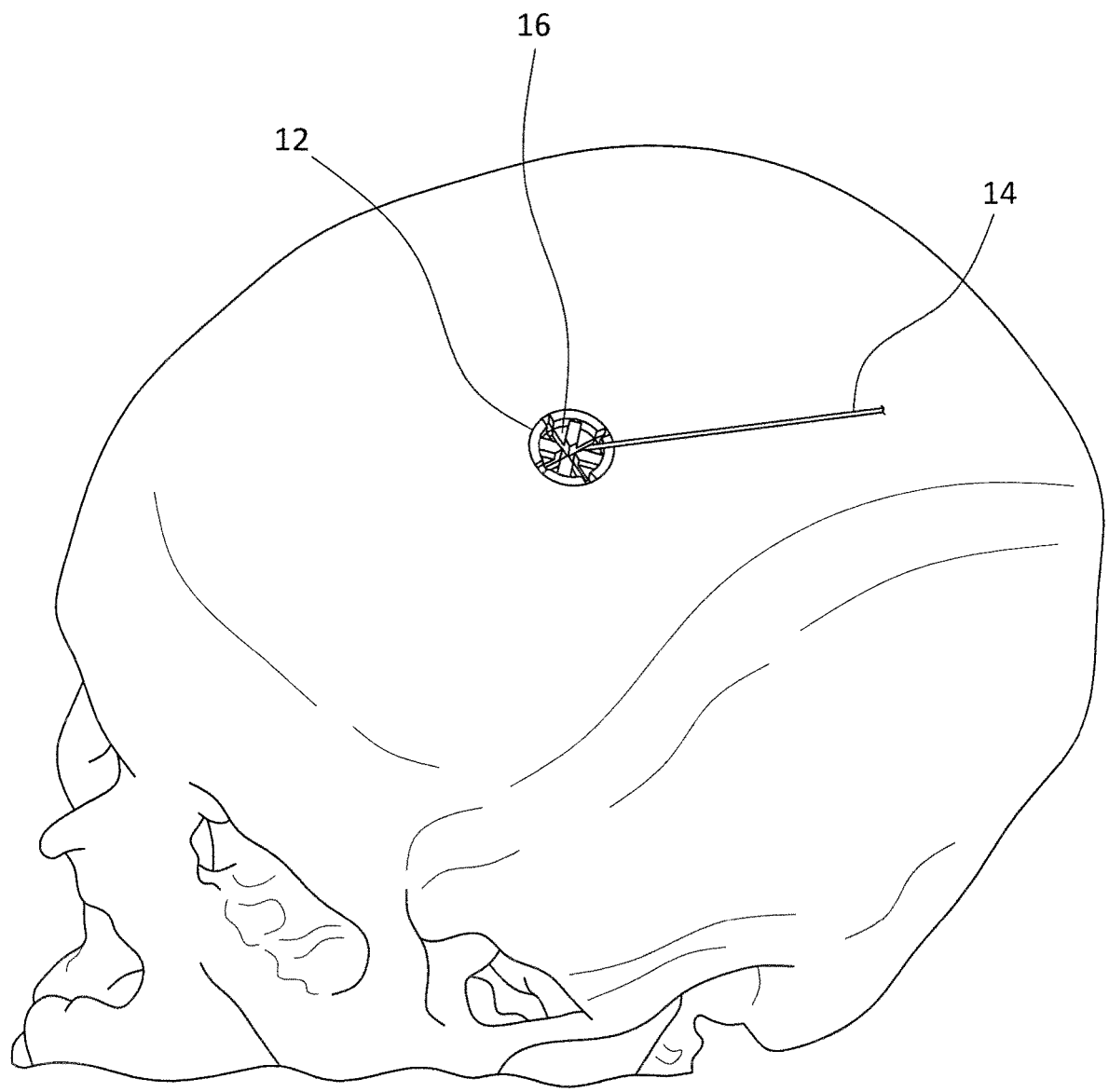
Figure 4:
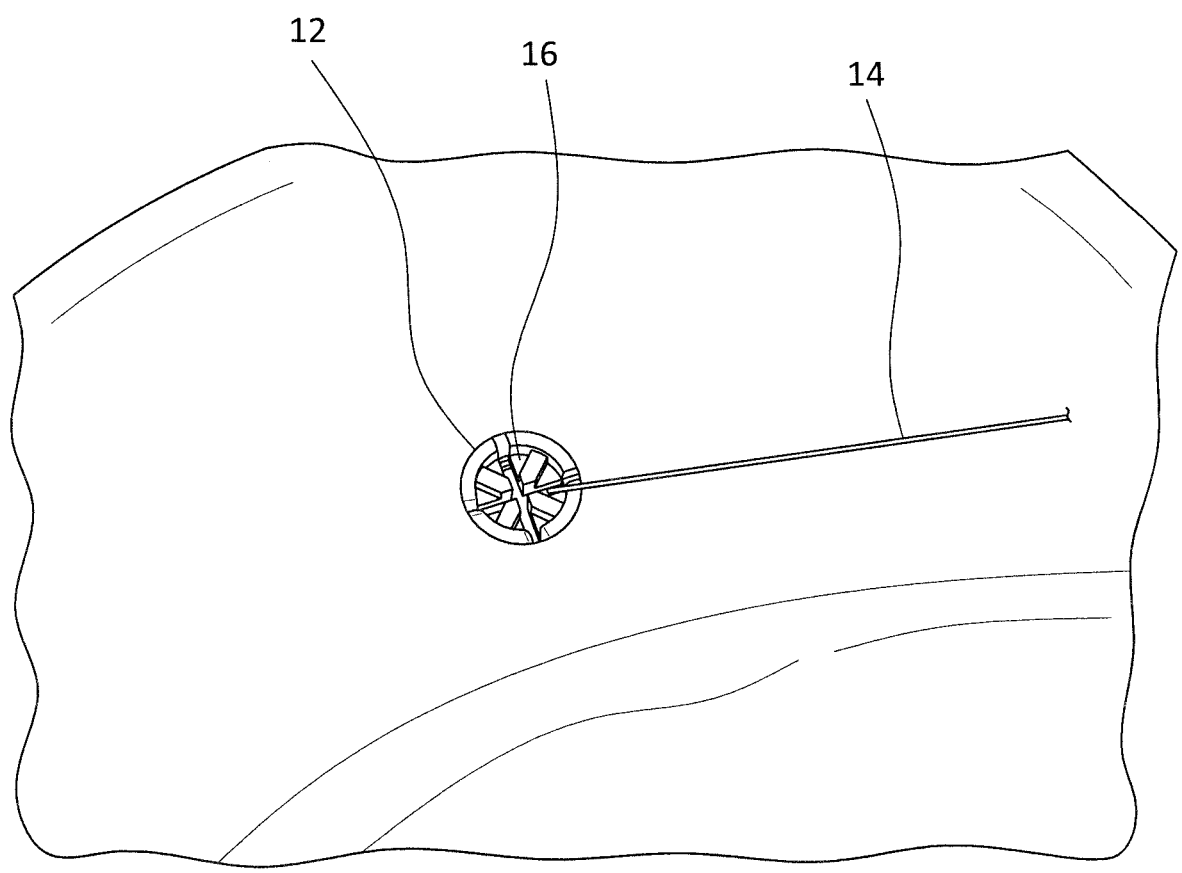
Figure 5:
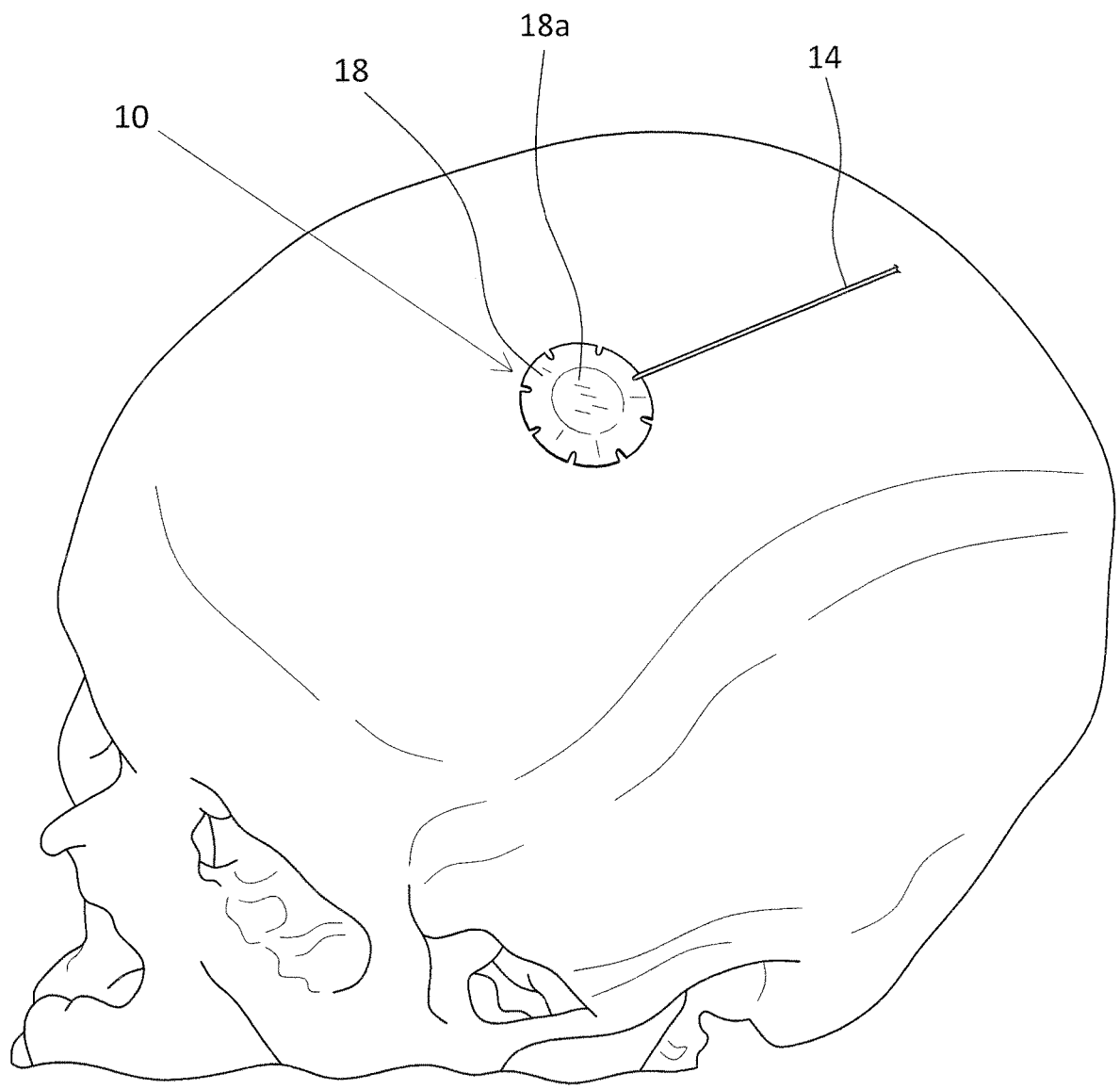

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

Referring to the figures, various embodiments for a burr hole plug 10 are disclosed. As those skilled in the art will appreciate, burr hole plugs are used in conjunction with a variety of surgical procedures requiring access to the brain. The procedures generally require the formation of a "burr hole" 12 within the cranium. The burr hole 12 allows surgeons to access the brain for the desired procedure. For example, burr holes 12 are commonly used in conjunction with deep brain stimulation procedures a stimulation lead 14 is implanted within the brain to position electrodes adjacent predetermined tissue of the brain. The electrodes are then used to electrically stimulate the tissue of the brain for treatment of a specific disease or disorder.

As those skilled in the art appreciate, the stimulation lead 14 is commonly passed through a burr hole 12. It is often necessary to keep the stimulation lead 14 in position for an extended period of time. As such, it is important that the burr hole 12 be covered and that the stimulation lead 14 be securely retained in position during this period of time. The present burr hole plug 10 provides a convenient, reliable, and effective solution to both covering the burr hole 12 and maintaining the stimulation lead 14 in position.

Referring to FIGS. 2 to 13, the burr hole plug 10 includes base member 16 and a cover member 18. As will be explained below in detail, the base member 16 is shaped and dimensioned for position withing the aperture defined by the burr hole 12 and die cover member 18 is shaped and dimensioned for placement over the base member 16 to fully close the burr hole 12 and retain a stimulation lead 14 passing through the burr hole plug 10 in place. In addition to retaining a stimulation lead 14 passing through the burr hole, the base member 16 and cover member 18 define a cavity allowing for wire management by storing excess lengths of stimulation leads 14 within the cavity defined by the base member 16 and the cover member 18. It should also be appreciated that while the embodiments disclosed below are circular, the burr hole plug could be formed in other shapes while taking advantage of the features offered by the present burr hole plug.

The base member 16 is substantially cylindrical and includes an annular frame member 20 defining the outer perimeter of the base member 16. The annular frame member 20 includes an upper surface 20a, a lower surface 20b, an inner sidewall 20c extending between the upper surface 20a and the lower surface 20b along the aperture 22 defined by the interior of the annular frame member 20, and an outer sidewall 20d extending between the upper surface 20a and the lower surface 20b of the annular frame member 20. In accordance with a disclosed embodiment, the upper portion 21a of the outside sidewall 20d defines a continuous diameter, while the lower portion 21b of the outer sidewall 20d tapers inwardly such that the diameter of the lower portion 21b decreases as it extends toward the lower surface 20b of the annular frame member. This taper helps to guide the base member 16 into the burr hole 12 as it is pressed into the burr hole 12. Further, and considering the inner sidewall 20c, it exhibits a constant diameter as it extends from the upper surface 20a to the lower surface 20b.

The base member 16 further includes a plurality of inwardly directed, triangular flange members 24a, 24b, 24c, 24d extending inwardly from the inner sidewall 20c toward the center of the annular frame member 20. Each of the flange members 24a, 24b, 24c, 24d includes an upper surface 26a and a lower surface 26b. First, second, and third edges 28a, 28b, 28c of the flange member 24a, 24b, 24c, 24d extend between the upper surface 26a and lower surface 26b. The first edge 28a of the flange member 24a, 24b, 24c, 24d is secured to the inner sidewall 20c, while the second edge 28b and the third edge 28c of the flange member 24a, 24b, 24c, 24d extend from the inner sidewall 20c to an apex 30 of the flange member 24a, 24b, 24c, 24d where the first and second edges 28b, 28c meet. In accordance with a disclosed embodiment, the apex 30 is slightly curved to allow for ease in the manipulation of the stimulation lead 14 as it passes therethrough.

In accordance with a disclosed embodiment, the base member 16 is provided with four flange members 24a, 24b, 24c, 24d symmetrically positioned within the annular frame member 20, with space provided between adjacent flange members 24a, 24b, 24c, 24d. The flange members 24a, 24b, 24c, 24d also lie in the same plane as they are mounted within the aperture defined by the annular frame member 20.

As such, and considering the space between adjacent edges 28b, 28c of the first, second, third, and fourth flange members 24a, 24h, 24c, 24d, the edges 28b, 28c of the first, second, third, and fourth flange members 24a, 24b, 24c, 24d define first, second, third, and fourth radially oriented passageways 32a, 32b, 32c, 32d. The radially oriented passageways 32a, 32b, 32c, 32d are shaped as spokes and extend from the annular frame member 20 toward the center of the base member 16 where they meet to define a central passageway 34.

At the position where each of the radially oriented passageways 32a, 32b, 32c, 32d meet annular frame member 20, the annular frame member 20 includes a cutout section 36a, 36b, 36c, 36d such that the open space defined by the radially oriented passageways 32a, 32b, 32c, 32d may extend through the annular frame member 20. As will be appreciated based upon the following disclosure, this allows for the passage of the stimulation lead 14 through the annular frame member 20 and out of the space defined by the base member 16.

Each flange member 24a, 24b, 24c, 24d is further provided with a support beam 38a, 38b, 38c, 38d along its upper surface. The support beam 38a, 38b, 38c, 38d radial extends from the first edge of the flange member 24a, 24b, 24c, 24d, where it is coupled to the inner sidewall 20c of the annular frame member 20, toward the apex 30 of the flange member 24a, 24b, 24c, 24d. In addition to providing for the structural integrity of the flange member 24a, 24b, 24c, 24d, the support beam 38a, 38b, 38c, 38d also assists in securing the cover member 18 in place and in holding the stimulation lead 14 in a desired orientation.

While a spoke configuration with four radially oriented passageways is disclosed above, it is appreciated the number of passageways and the orientation of the passageways may be varied to suit specific needs. It is, however, appreciated the construction of the base member 16 and the flange members 24a, 24b, 24c, 24d integrated therewith are designed to optimize the structural stability of the base member 16 so that is properly flexes as it is positioned with the burr hole 12. Considering the base member 16 is dimensioned for frictional engagement with the inner wall of the burr hole 12 and is, therefore, subjected to inwardly directed forces as it is forced within the burr hole 12, the base member 16 must be constructed to withstand such forces so as not substantially maintain its circular configuration. The construction of the base member 16 to allow for slight compression as it is inserted into the burr hole 12 is further enhanced by the cutout section 36a, 36b, 36c, 36d discussed above. In addition to allowing for the passage of the stimulation lead 14 through the annular frame member 20 and out of the space defined by the base member 16, the cutout section 36a, 36b, 36c, 36d also provide for compression of the base member without the formation of ridges along the outer sidewall 20d.

Figure 14:
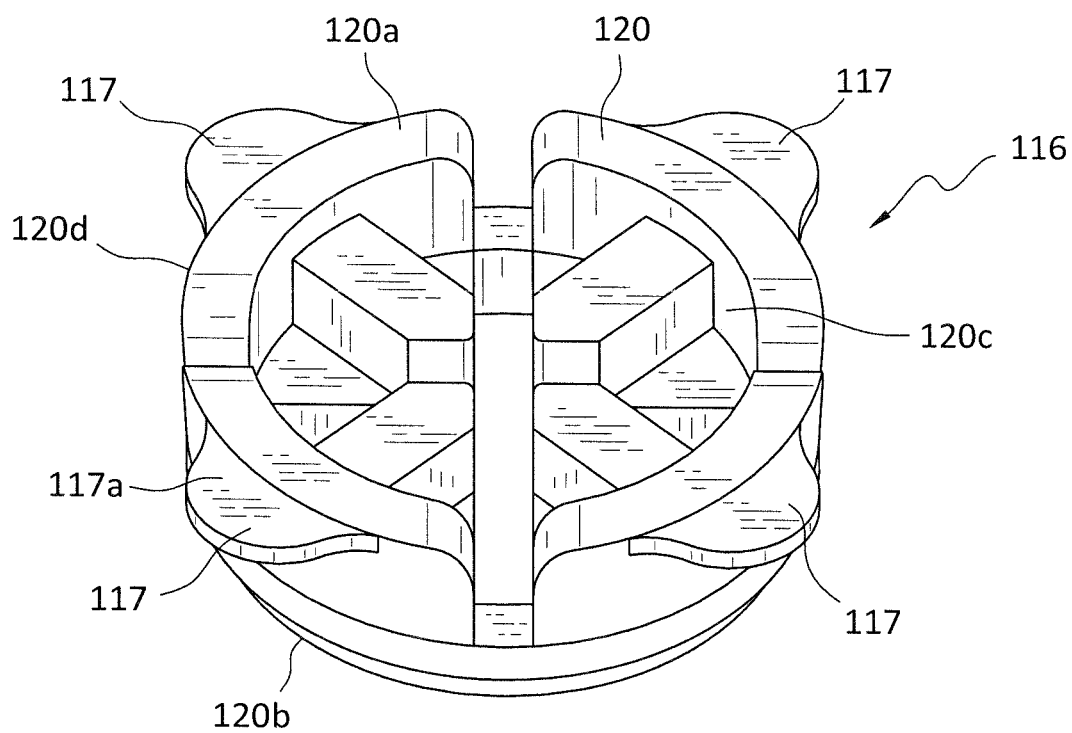
FIGS. 14, 15, and 16 are respectively a top perspective view, a top plan view and a side elevation view of the base member in accordance with an alternate embodiment.
Figure 15:
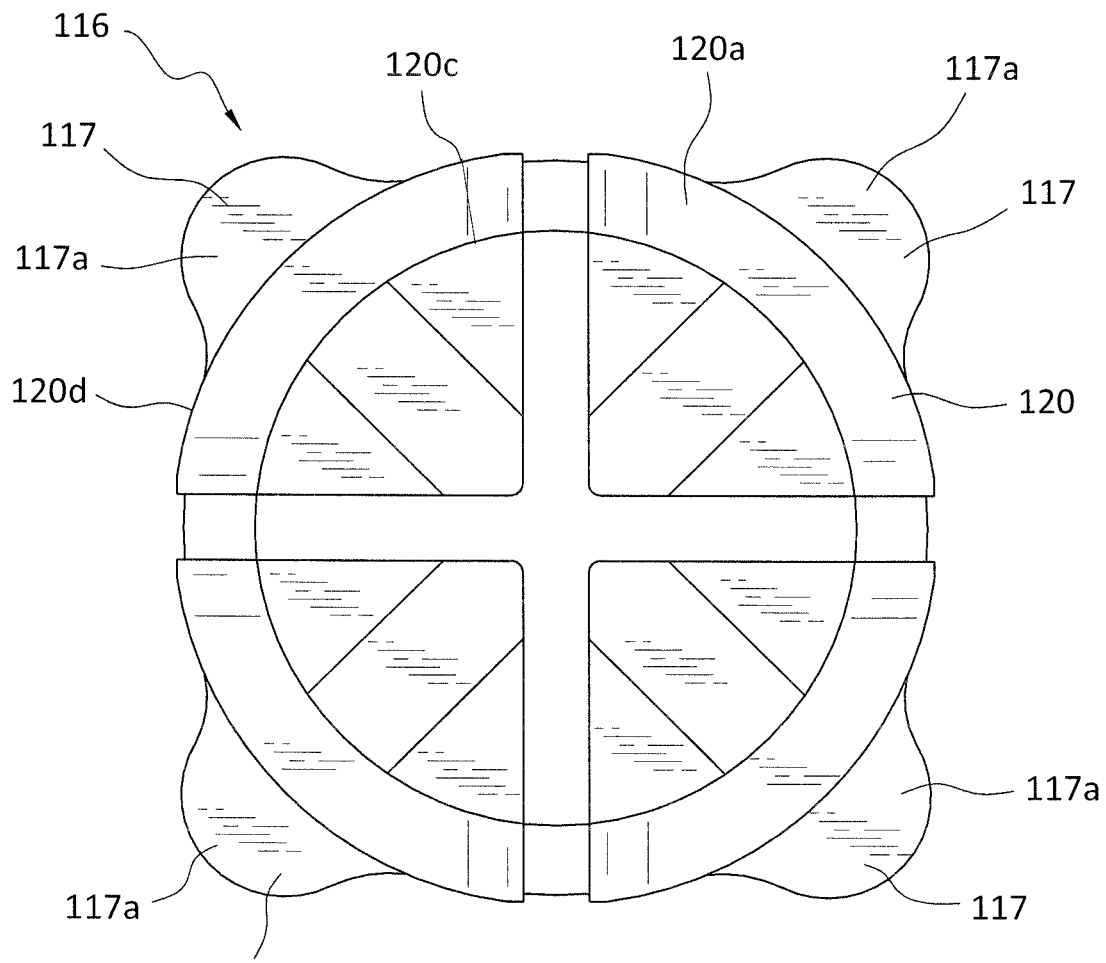
Figure 16:
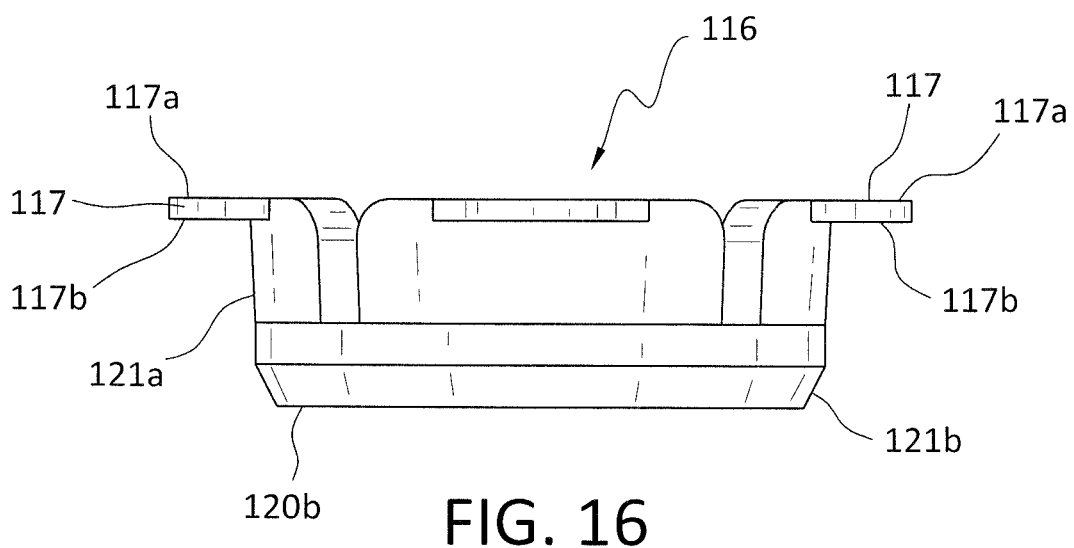

In accordance with an alternate embodiment, and with reference to FIGS. 14 to 16, the base member 116 may be constructed with outwardly extending tab or flange member 117 to prevent the base member 116 from "plunging" into the burr hole in the event the burr hole is flawed or if inadvertent force is applied to the burr hole plug causing it to move through the burr hole and into the intracranial space.

In accordance with such an embodiment, the structure within the annular frame member 120 remains the same as the embodiment described above and will not be repeated herein. As to the remainder of this alternate embodiment of the base member 116, it includes an annular frame member 120 defining the outer perimeter of the base member 116. The annular frame member 120 includes an upper surface 120a, a lower surface 120b, an inner sidewall 120c extending between the upper surface 120a and the lower surface 120b along the aperture 122 defined by the interior of the annular frame member 120, and an outer sidewall 120d extending between the upper surface 120a and the lower surface 120b of the annular frame member 120. As with prior embodiment, the upper portion 121a of the outer sidewall 120d defines a continuous diameter, while the lower portion 121b of the outer sidewall 120d tapers inwardly such that the diameter of the lower portion 121b decreases as it extends toward the lower surface 120b of the annular frame member 120.

Extending radially outwardly from the outer sidewall 120d of the annular frame member 120 adjacent the upper surface 120a thereof are a plurality of tab (or flange) members 117. The tab members 117 extend a small distance beyond the outer circumference of the annular frame member 120 as defined by the outer sidewall 120d of the annular frame member 120. The tab members 117 are shaped and dimensioned to prevent the base member 116 from "plunging" through the burr hole and into the intercranial space in the event the burr hole is flawed or if inadvertent force is applied thereto. As such, and in accordance with a disclosed embodiment, each of the tab members 117 include upper and lower surfaces 117a, 117b wherein the upper surface 117a lies in approximately the same plane as the upper surface 120a of the annular frame member 120 and the lower surface 117b of the tab member 117 is placed in direct contact with the outer surface of the cranium. The tab member 117 is thin so that it does not protrude far from the outer surface of the cranium.

As to the internal structure of the base member 16, and as mentioned above, it is the same as the embodiment discussed above with reference to FIGS. 6, 8, and 9.

The base member 16 is preferably made of porous polyethylene. However, it is appreciated other materials, for example, expanded polytetrafluoroethylene (EPTFE), silicone, polymethyl methacrylate (PMMA), polyether ether ketone (PEEK), or other biocompatible materials may be used in construction of the base member 16 so long as they offer similar material properties.

The cover member 18 is generally disk shaped and includes an upper surface 18a, a lower surface 18b, and a perimeter sidewall 18c extending between the upper surface 18a and the lower surface 18b along edge of the cover member 18. The upper surface 18a is generally smooth, while the lower surface 18b is shaped and dimensioned for engagement with the base member 16 for the purpose of both securely holding the cover member 18 and the base member 16 together and securely retaining the stimulation lead 14 as it passes through the burr hole 12 and the burr hole plug 10. As will be appreciated based upon the following disclosure, the cover member 18 has a diameter that is larger than that of the base member 16. As such, the cover member 18 sits completely over the base member 16 and those portions of the cover member 18 extending beyond the base member 16 lie upon the skull.

In particular, lower surface of the cover member 18 is formed with a plurality of radially extending slots 40. The slots 40 are oriented as spokes that extend from the outer perimeter sidewall 18c and that terminate at a central cavity 42 located at the center of the cover member 18. Although there are disclosed four flange members 24 in accordance with the embodiment of the base member 16 described above, there are six radially extending slots 40 symmetrically positioned along the lower surface 18b of the cover member 18. Both the widths of the slots 40 of the cover member 18 and the radially oriented passageways 32a, 32b, 32c, 32d of the base member 16 are selected to provide a suitable area within which the stimulation lead 14 may be positioned.

The edge of the cover member 18 is further provided with small cutouts 44 in alignment with the radially extending slots 40. These cutouts 44 allow for enhanced cable management as the stimulation lead 14 extends from the brain, through the burr hole plug 10 and out of the burr hole plug 10. The cutouts 44 provide a pathway guiding the stimulation leads 14 from the passageways 32a, 32b, 32c, 32d, past the annular frame member 20, and to the outer edge of the cover member 18 where the stimulation leads may be guided for connection with various neurosurgical functional devices.

Secure attachment of the cover member 18 with the base member 16 is facilitated by the provision of a downwardly extending flange member 46 along the lower surface 18b of the cover member 18. The downwardly extending flange member 46 is shaped and dimensioned to frictionally engage the upper edge 48 of the annular frame member 20 where in the upper surface 20a and the inner sidewall. 20c thereof meet. With this in mind, the flange members 24a, 24b, 24c, 24d are positioned slightly lower than the upper surface 20a of the annular frame member 20 so as to allow for positioning of the downwardly extending flange member 46 slightly within the cavity defined by the base member 16 as the cover member 18 is pressed downwardly into the base member 16 such that the downwardly extending flange member 46 engages the upper edge 48 of the annular frame member 20.

While frictional connection between the cover member 18 and the base member 16 is disclosed above, it is appreciated other coupling mechanisms could be employed. For example, the cover member could be directly attached to the skull via screws passing though the outer edges of the cover member or screws could be used to attach the cover member to the base member. Further, adhesive could be used to secure the cover member to the base member.

The cover member 18 is preferably made of porous polyethylene. However, it is appreciated other materials, for example, titanium, expanded polytetrafluoroethylene (EPTFE), silicone, polymethyl methacrylate (PMMA), polyether ether ketone (PEEK), or other biocompatible materials may be used in construction of the cover member 18 so long as they offer similar material properties. While a disclosed embodiment, uses porous polyethylene for both the base member and the cover member, it is appreciated variations in the materials may offer advantages for various applications. For example, where it is desirable to allow for tissue in-growth in the base member while preventing tissue in-growth in the cover member, it might be desirable to make the base member from porous polyethylene and make the cover member from titanium.

In practice, and with reference to FIGS. 2 to 5, after the burr hole 12 is created in a standard manner using a perforator bit. As is customary when using a perforator bit, the burr hole 12 is drilled in a manner forming an inwardly directed lip 13 along the lower edge of the burr hole. The drilling technique ensures that the perforator bit does not fully penetrate the skull and enter the brain. In a typical procedure, the lip is then removed, but the present procedure retains the lip and uses it to ensure proper positioning of the base member 16.

The base member 16 is positioned within the aperture defining the burr hole 12 and pressed downwardly into the burr hole 12 until the lower surface 20b contracts the inwardly directed lip 13 and further downward movement is resisted. This allows the base member 16 to be inserted without worrying that it will be pushed through the burr hole 12 The base member 16 is shaped and sized to frictionally secure itself to the inner wall of the burr hole 12 as it is pushed into the burr hole. While frictional attachment of the base member 16 within the burr hole 12 is disclosed in accordance with an embodiment, it is appreciated other fastening techniques may be employed without departing from the spirit of the invention. For example, the base member 16 could be provided with outwardly extending tabs that are secured to the skull via screws.

Once the base member 16 is positioned within the burr hole 12, the stimulation lead 14 is passed therethrough and positioned at desired location within the brain. It is also appreciated that the stimulation lead 14 may be passed through the burr hole 12 prior to placement of the base member 16 and the base member 16 would then be passed over the stimulation lead 14 prior to positioning of the base member 16 within the burr hole 12. The portion of the stimulation lead 14 passing through the base member 16 may then be moved into the closest or most convenient radially oriented passageway 32a, 32b, 32c, 32d. The radially oriented passageways 32a, 32b, 32c, 32d are such a size that they frictionally engage the outer surface of the stimulation lead 14 to hold it in place within the radially oriented passageways 32a, 32b, 32c, 32d. The remainder of the stimulation lead 14 that is within the base member 16 may then be passed through the cutout sections 36a, 36b, 36c, 36d along the annular frame member 20 such that the stimulation lead 14 extends out of the space defined by base member 16.

Thereafter, the cover member 18 is positioned over the base member 16 with at least one of the slots 40 in alignment with the stimulation lead 14. The cover member 18 is then pressed downwardly until the downwardly extending flange member 46 of the cover member 18 frictional engages the upper edge 48 of the annular frame member 20.

Figure 6:
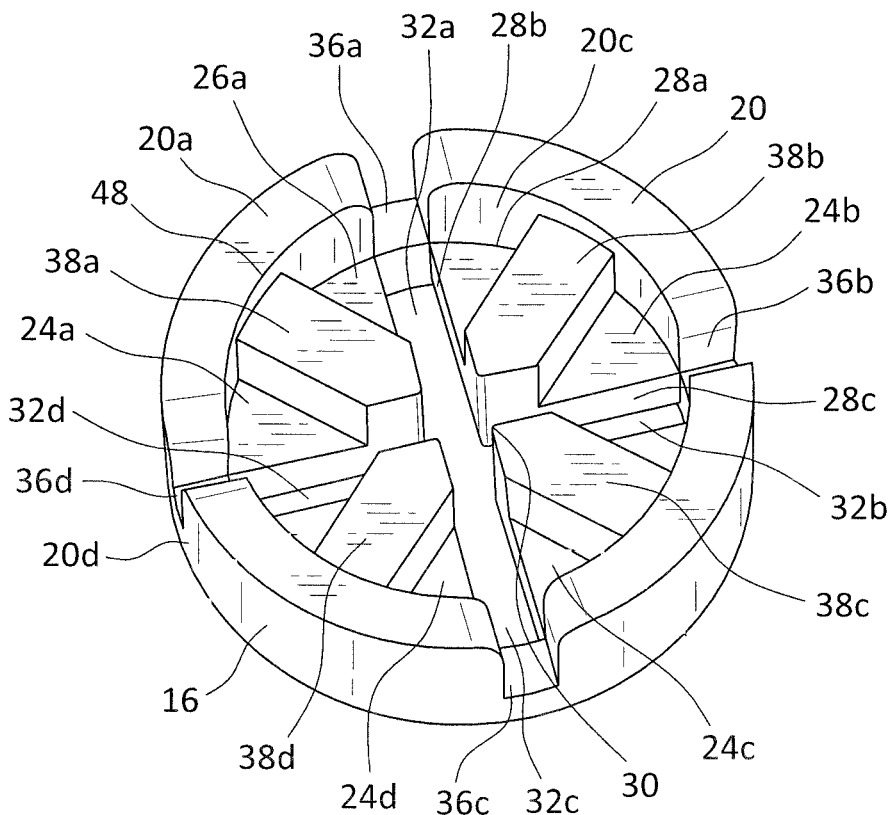
FIG. 6 is a perspective view of the base member of the burr hole plug.
Figure 7:
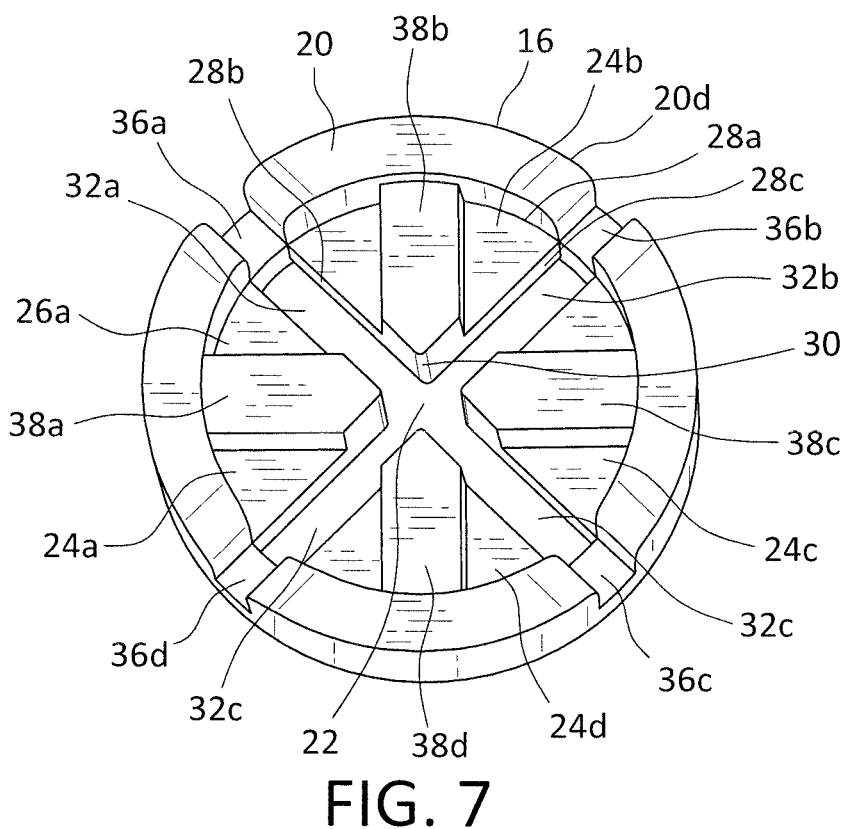
FIG. 7 is a top plan view of the base member.
Figure 8:
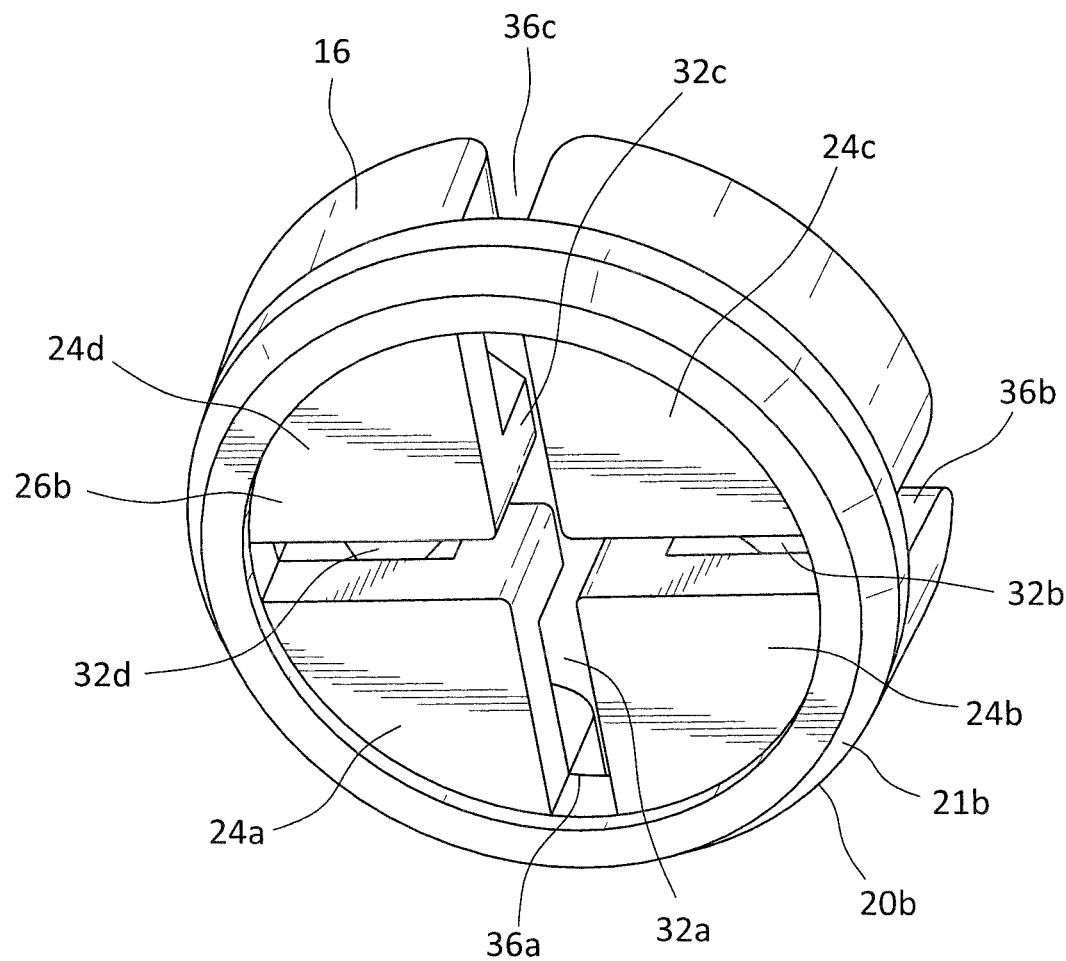
FIG. 8 is a bottom perspective view of the base member.
Figure 9:
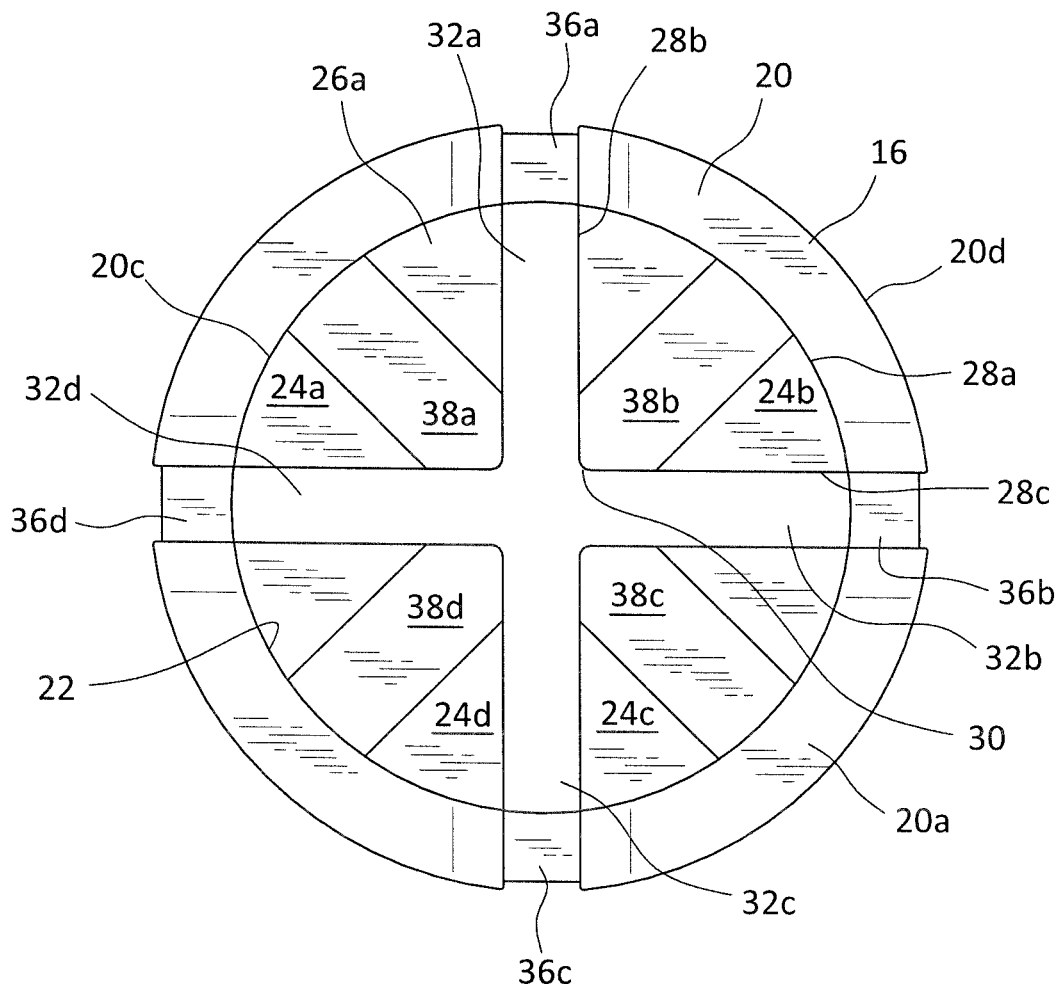
FIGS. 9 and 10 are respectively a top plan view and a side elevation view of the base member.
Figure 10:
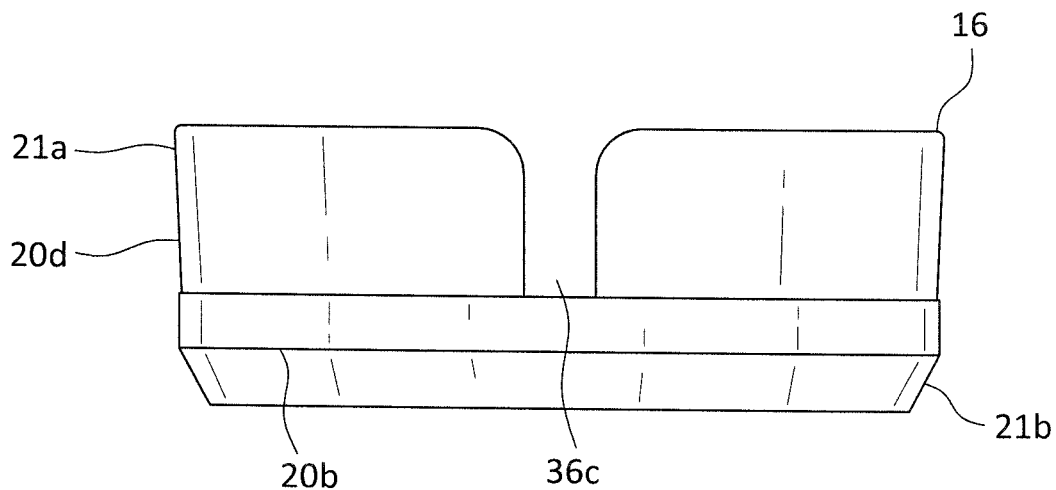
Figure 11:
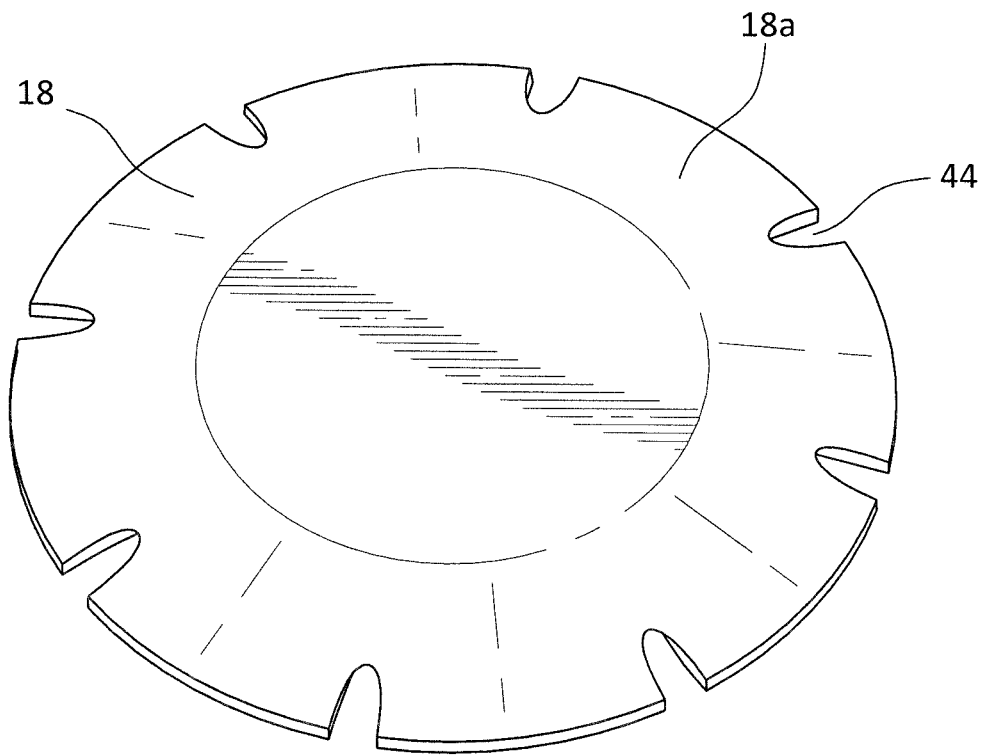
FIG. 11 is a top perspective view of the cover member of the burr hole plug.
Figure 12:
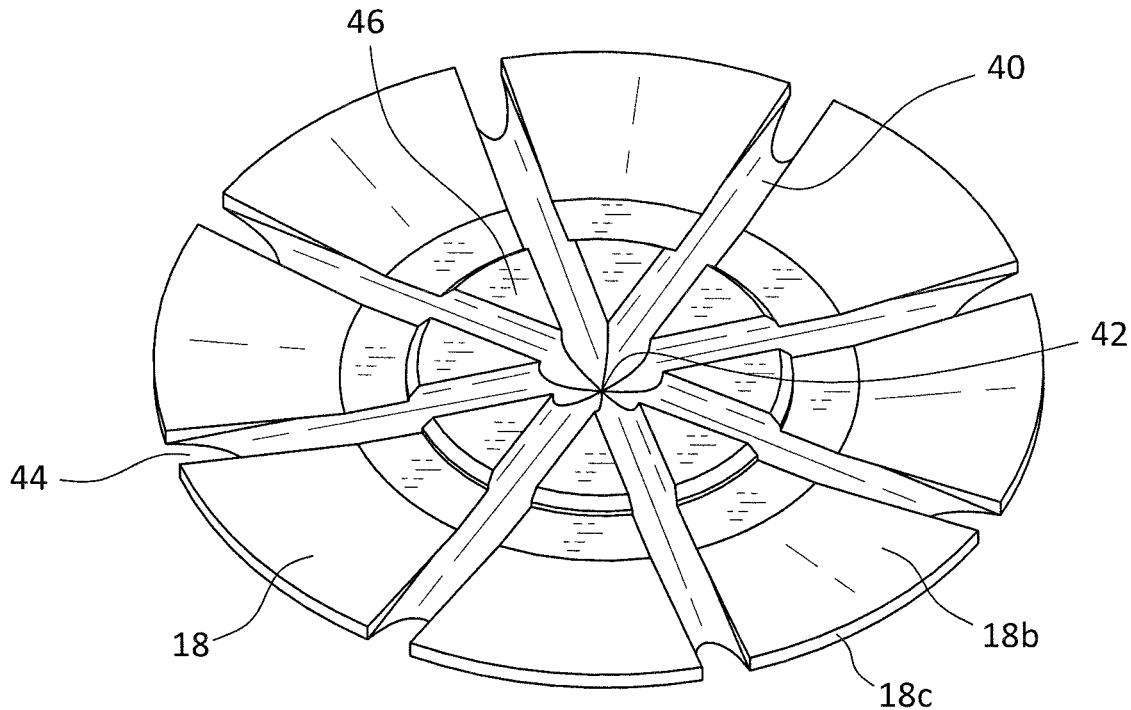
FIG. 12 is a bottom perspective view of the cover member.
Figure 13:
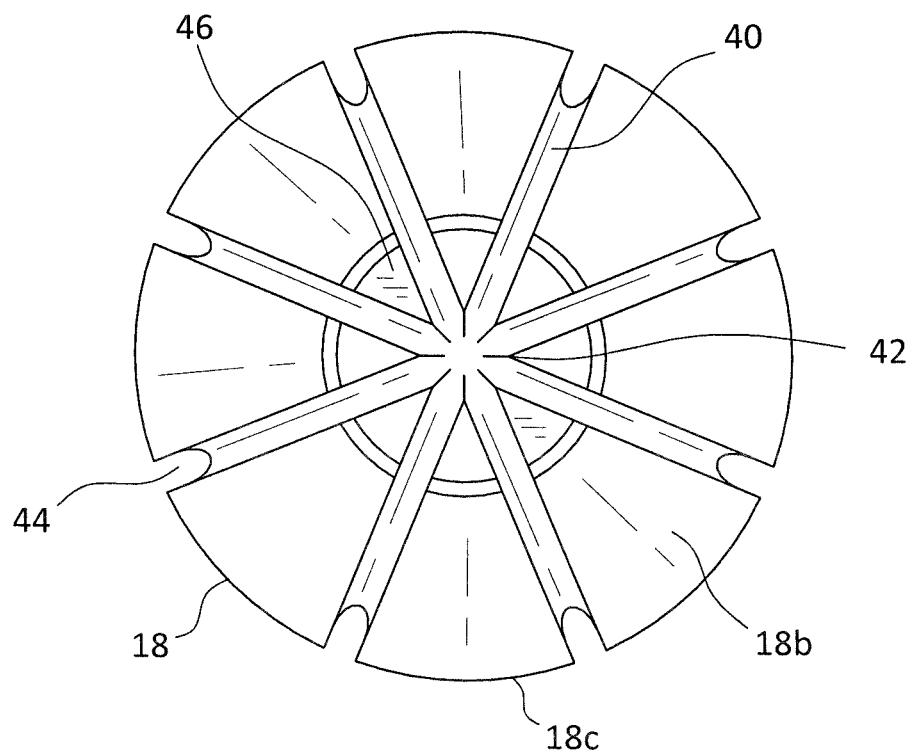
FIG. 13 is a bottom elevation view of the cover member.

The cover member s described above for use in conjunction with the base member disclosed with reference to FIGS. 6, 8, and 9. It is, however, appreciated the cover member may also be used in conjunction with the embodiment of the base member disclosed with reference to FIGS. 10 to 12. Where the base member disclosed with reference to FIGS. 10 to 12 is used, it is contemplated that the lower surface of the cover member may be contoured to enhance the placement of the cover member over the base member.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A burr hole plug, comprising:
a base member that is substantially cylindrical and is shaped and dimensioned for positioning within an aperture defined by a burr hole, the base member includes an annular frame member defining an outer perimeter of the base member, the annular frame member further includes at least one cutout section such that open space defined by the radially oriented passageways extends through the annular frame member to allow for the passage of a stimulation lead through the annular frame member and out of the base member, and the base member includes at least one passageway for passage of stimulation leads through the base member, the at least one passageway is defined by a plurality of inwardly directed flange members extending inwardly from the annular frame member toward a center of the annular frame member, wherein each of the plurality of inwardly directed flange members includes an upper surface, a lower surface, edges, and an apex, wherein adjacent edges of the plurality of inwardly directed flange members define radially oriented passageways that extend from the annular frame member toward the center of the base member where they meet to define a central passageway; and
a cover member shaped and dimensioned for placement over the base member to close the burr hole and retain a stimulation lead passing through the burr hole in place, wherein the cover member is disk shaped and includes an upper surface, a lower surface, and a perimeter sidewall extending between the upper surface and the lower surface along an edge of the cover member, wherein the lower surface of the cover member is formed with a plurality of radially extending slots that are oriented as spokes that extend from the perimeter sidewall and that terminate at a central cavity located at the center of the cover member.

2. The burr hole plug according to claim 1, wherein the annular frame member includes an upper surface, a lower surface, an inner sidewall extending between the upper surface and the lower surface along an aperture defined by an interior of the annular frame member, and an outer sidewall extending between the upper surface and the lower surface of the annular frame member.

3. The burr hole plug according to claim 1, wherein each flange member is provided with a support beam along its upper surface.

4. The burr hole plug according to claim 1, wherein the base member includes an outwardly extending tab member to prevent the base member from plunging into the burr hole.

5. The burr hole plug according to claim 1, wherein the base member is made of porous polyethylene, expanded polytetrafluoroethylene, silicone, polymethyl methacrylate, or polyether ether ketone.

6. The burr hole plug according to claim 5, wherein the cover member is made of porous polyethylene, titanium, expanded polytetrafluoroethylene, silicone, polymethyl methacrylate, or polyether ether ketone.

7. The burr hole plug according to claim 6, wherein the base member and cover member are made of different materials.

8. A burr hole plug, comprising:
a base member that is substantially cylindrical and is shaped and dimensioned for positioning within an aperture defined by a burr hole, the base member includes an annular frame member defining an outer perimeter of the base member, the annular frame member further includes at least one cutout section such that open space defined by the radially oriented passageways extends through the annular frame member to allow for the passage of a stimulation lead through the annular frame member and out of the base member, and the base member includes at least one passageway for passage of stimulation leads through the base member, the at least one passageway is defined by a plurality of inwardly directed flange members extending inwardly from the annular frame member toward a center of the annular frame member, wherein each of the plurality of inwardly directed flange members includes an upper surface, a lower surface, edges, and an apex, wherein adjacent edges of the plurality of inwardly directed flange members define radially oriented passageways that extend from the annular frame member toward the center of the base member where they meet to define a central passageway; and
a cover member shaped and dimensioned for placement over the base member to close the burr hole and retain a stimulation lead passing through the burr hole in place, wherein the cover member is disk shaped and includes an upper surface, a lower surface, and a perimeter sidewall extending between the upper surface and the lower surface along an edge of the cover member, wherein the lower surface of the cover member is formed with a plurality of radially extending slots, wherein the edge of the cover member is further provided with cutouts in alignment with the radially extending slots.

9. The burr hole plug according to claim 8, wherein the annular frame member includes an upper surface, a lower surface, an inner sidewall extending between the upper surface and the lower surface along an aperture defined by an interior of the annular frame member, and an outer sidewall extending between the upper surface and the lower surface of the annular frame member.

10. The burr hole plug according to claim 8, wherein each flange member is provided with a support beam along its upper surface.

11. The burr hole plug according to claim 8, wherein the base member includes an outwardly extending tab member to prevent the base member from plunging into the burr hole.

12. The burr hole plug according to claim 8, wherein the base member is made of porous polyethylene, expanded polytetrafluoroethylene, silicone, polymethyl methacrylate, or polyether ether ketone.

13. The burr hole plug according to claim 12, wherein the cover member is made of porous polyethylene, titanium, expanded polytetrafluoroethylene, silicone, polymethyl methacrylate, or polyether ether ketone.

14. The burr hole plug according to claim 13, wherein the base member and cover member are made of different materials.

15. The burr hole plug according to claim 8, wherein each flange member is provided with a support beam along its upper surface.

16. A burr hole plug, comprising:
a base member shaped and dimensioned for positioning within an aperture defined by a burr hole, the base member includes an annular frame member defining an outer perimeter of the base member and at least one passageway for passage of stimulation leads through the base member, the at least one passageway is defined by a plurality of inwardly directed flange members extending inwardly from the annular frame member toward a center of the annular frame member, wherein each of the plurality of inwardly directed flange members includes an upper surface, a lower surface, edges, and an apex, wherein adjacent edges of the plurality of inwardly directed flange members define radially oriented passageways that extend from the annular frame member toward the center of the base member where they meet to define a central passageway; and
a cover member shaped and dimensioned for placement over the base member to close the burr hole and retain a stimulation lead passing through the burr hole in place, the cover member is disk shaped and includes an upper surface, a lower surface formed with a plurality of radially extending slots, and a perimeter sidewall extending between the upper surface and the lower surface along an edge of the cover member, wherein the slots are oriented as spokes that extend from the perimeter sidewall and that terminate at a central cavity located at a center of the cover member.

17. The burr hole plug according to claim 16, wherein the annular frame member includes an upper surface, a lower surface, an inner sidewall extending between the upper surface and the lower surface along an aperture defined by an interior of the annular frame member, and an outer sidewall extending between the upper surface and the lower surface of the annular frame member.

18. The burr hole plug according to claim 16, wherein each flange member is provided with a support beam along its upper surface.

19. The burr hole plug according to claim 16, wherein the base member includes an outwardly extending tab member to prevent the base member from plunging into the burr hole.

20. The burr hole plug according to claim 16, wherein the base member is made of porous polyethylene, expanded polytetrafluoroethylene, silicone, polymethyl methacrylate, or polyether ether ketone.

21. The burr hole plug according to claim 20, wherein the cover member is made of porous polyethylene, titanium, expanded polytetrafluoroethylene, silicone, polymethyl methacrylate, or polyether ether ketone.

22. The burr hole plug according to claim 21, wherein the base member and cover member are made of different materials.

23. A burr hole plug, comprising:
a base member shaped and dimensioned for positioning within an aperture defined by a burr hole, the base member includes an annular frame member defining an outer perimeter of the base member and at least one passageway for passage of stimulation leads through the base member, the at least one passageway is defined by a plurality of inwardly directed flange members extending inwardly from the annular frame member toward a center of the annular frame member, wherein each of the plurality of inwardly directed flange members includes an upper surface, a lower surface, edges, and an apex, wherein adjacent edges of the plurality of inwardly directed flange members define radially oriented passageways that extend from the annular frame member toward the center of the base member where they meet to define a central passageway; and
a cover member shaped and dimensioned for placement over the base member to close the burr hole and retain a stimulation lead passing through the burr hole in place, the cover member is disk shaped and includes an upper surface, a lower surface formed with a plurality of radially extending slots, and a perimeter sidewall extending between the upper surface and the lower surface along an edge of the cover member The burr hole plug according to claim 16, wherein the edge of the cover member is further provided with cutouts in alignment with the radially extending slots.

24. The burr hole plug according to claim 23, wherein the annular frame member includes an upper surface, a lower surface, an inner sidewall extending between the upper surface and the lower surface along an aperture defined by an interior of the annular frame member, and an outer sidewall extending between the upper surface and the lower surface of the annular frame member.

25. The burr hole plug according to claim 23, wherein the base member includes an outwardly extending tab member to prevent the base member from plunging into the burr hole.

26. The burr hole plug according to claim 23, wherein the base member is made of porous polyethylene, expanded polytetrafluoroethylene, silicone, polymethyl methacrylate, or polyether ether ketone.

27. The burr hole plug according to claim 26, wherein the cover member is made of porous polyethylene, titanium, expanded polytetrafluoroethylene, silicone, polymethyl methacrylate, or polyether ether ketone.

28. The burr hole plug according to claim 27, wherein the base member and cover member are made of different materials.

* * * * *

UNITED STATES PATENT AND TRADEMARK OFFICE
CERTIFICATE OF CORRECTION

| | | |
|---|---|---|
| PATENT NO. | : 12,128,232 B2 | Page 1 of 1 |
| APPLICATION NO. | : 17/643508 | |
| DATED | : October 29, 2024 | |
| INVENTOR(S) | : Clawson et al. | |

It is certified that error appears in the above-identified patent and that said Letters Patent is hereby corrected as shown below:

On the Title Page

Item (72), add:
Zachary T. Levine, Teaneck, NJ (US).

Signed and Sealed this
Fifteenth Day of July, 2025

Coke Morgan Stewart
*Acting Director of the United States Patent and Trademark Office*